United States Patent [19]

VandenBerg

[11] Patent Number: Plant 6,771

[45] Date of Patent: May 2, 1989

[54] CHRYSANTHEMUM PLANT NAMED DALVINA

[75] Inventor: Cornelis P. VandenBerg, Salinas, Calif.

[73] Assignee: Yoder Brothers, Inc., Barberton, Ohio

[21] Appl. No.: 135,293

[22] Filed: Dec. 21, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Dalvina particularly characterized by its flat capitulum form; daisy capitulum type; yellow ray floret color; diameter across face of capitulum of up to 8 cm at maturity when grown as a pinched spray pot mum; uniform eight week photoperiodic flowering response to short days; tall plant height when grown as a pinched pot mum; and semi-spreading branching pattern.

1 Drawing Sheet

The present invention comprises a new and distinct cultivar of Chrysanthemum, botanically known as *Chrysanthemum morifolium,* Ramat., and referred to by the cultivar name Dalvina.

Dalvina, identified as 83435017, was originated from a cross made by Cornelis P. VandenBerg in a controlled breeding program in Salinas, Calif. in 1983.

The female parent of Dalvina was the cultivar identified as Pert, disclosed in U.S. Plant Pat. No. 4,764. The male parent of Dalvina was the cultivar identified as Fiesta, disclosed in U.S. Plant Pat. No. 3,632.

Dalvina was discovered and selected as one flowering plant within the progeny of the stated cross by Cornelis P. VandenBerg in July of 1983, in a controlled environment in Salinas, Calif.

The first act of asexual reproduction of Dalvina was accomplished when vegetative cuttings were taken from the initial selection in September of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dalvina are firmly fixed and are retained through successive generations of asexual reproduction.

Dalvina has not been observed under all possible environmental conditions. The phenotype may vary significantly with variations in environment such as temperature, light intensity, and daylength.

The following observations, measurements and comparisons describe plants grown in Salinas, Calif. and Leaminton, Canada, under greenhouse conditions which approximate those generally used in commercial greenhouse practice.

The following traits have been repeatedly observed and are determined to be basic characteristics of Dalvina, which, in combination, distinguish this Chrysanthemum as a new and distinct cultivar:

1. Flat capitulum form.
2. Daisy capitulum type.
3. Yellow ray floret color.
4. Diameter across face of capitulum up to 8 cm at maturity when grown as a pinched spray pot mum.
5. Uniform eight week photoperiodic flowering response to short days.

6. Tall plant height, requiring 0 to 7 long days after pinch prior to short days and 1 to 2 applications of 2500 ppm B-9 SP to attain a flowered plant height of 25 to 35 cm for year-round flowerings when grown as a pinched pot mum.
7. Semi-spreading branching pattern.

The accompanying photographic drawings show typical inflorescence and leaf characteristics of Dalvina, with the colors being as nearly true as possible with illustrations of this type.

Sheet 1 is a color photograph of Dalvina grown as a pinched spray pot mum.

Sheet 2 is a black and white photograph of three views of the inflorescence of Dalvina.

Sheet 3 is a black and white photograph showing the upper and under sides of the leaves of Dalvina at three stages of development (mature, intermediate and immature).

Of the commercial cultivars known to the inventor, the most similar in comparison to Dalvina is the female parent Pert. Reference is made to attached Chart A, which compares certain characteristics of Dalvina to the same characteristics of Pert.

Similar traits are capitulum form and type, branching pattern and flowering response period. Dalvina is slightly lighter in ray floret color, has a slightly smaller diameter of capitulum, and has a taller plant height than Pert.

In the following description, color references are made to The Royal Horticultural Society Colour Chart. The color values were determined on plant material grown as a pinched spray pot mum in Salinas, Calif. on Mar. 17, 1987.

Classification:

*Botanical.*—*Chrysanthemum morifolium,* Ramat., cv. Dalvina.

*Commercial.*—Daisy spray pot mum.

INFLORESCENCE

A. Capitulum:

*Form.*—Flat.

*Type.*—Daisy.

*Diameter across face.*—Up to 8 cm at maturity.

B. Corolla of ray florets:

*Color (general tonality from a distance of three meters).*—Yellow.

*Color (upper surface).*—5A.

*Color (under surface).*—5B.

*Shape.*—Oblong, slightly reflexing at maturity.

C. Corolla of disc florets:

*Color (mature).*—14A to 14B.

*Color (immature).*—Closest to 144B to 144C.

D. Reproductive organs:

*Androecium.*—Present on disc florets only; moderate pollen.

*Gynoecium.*—Present on both ray and disc florets.

PLANT

A. General appearance:

*Height.*—Tall; 25 to 35 cm as a pinched spray pot mum with 0 to 7 long days after pinch prior to short days and 1 to 2 applications of 2500 ppm B-9 SP.

*Branching pattern.*—Semi-spreading.

B. Foliage:

*Color (upper surface).*—147A.

*Color (under surface).*—147B.

*Shape.*—Deeply lobed and serrated.

CHART A

Comparison of Dalvina and Pert

| Cultivar | Ray Floret Color | Capitulum Form and Type | Branching Pattern |
|---|---|---|---|
| Dalvina | Yellow | Flat Daisy | Semi-spreading |
| Pert | Dark yellow | Flat Daisy | Semi-spreading |

| Cultivar | Diameter across face of capitulum | Plant height | Flowering response period |
|---|---|---|---|
| Dalvina | Up to 8 cm | Tall | 8 weeks |
| Pert | 70–90 mm | Short | 8 weeks |

Comparisons made of plants grown as pinched spray pot mums in Salinas, California

I claim:

1. A new and distinct Chrysanthemum plant named Dalvina, as described and illustrated, and parts thereof.

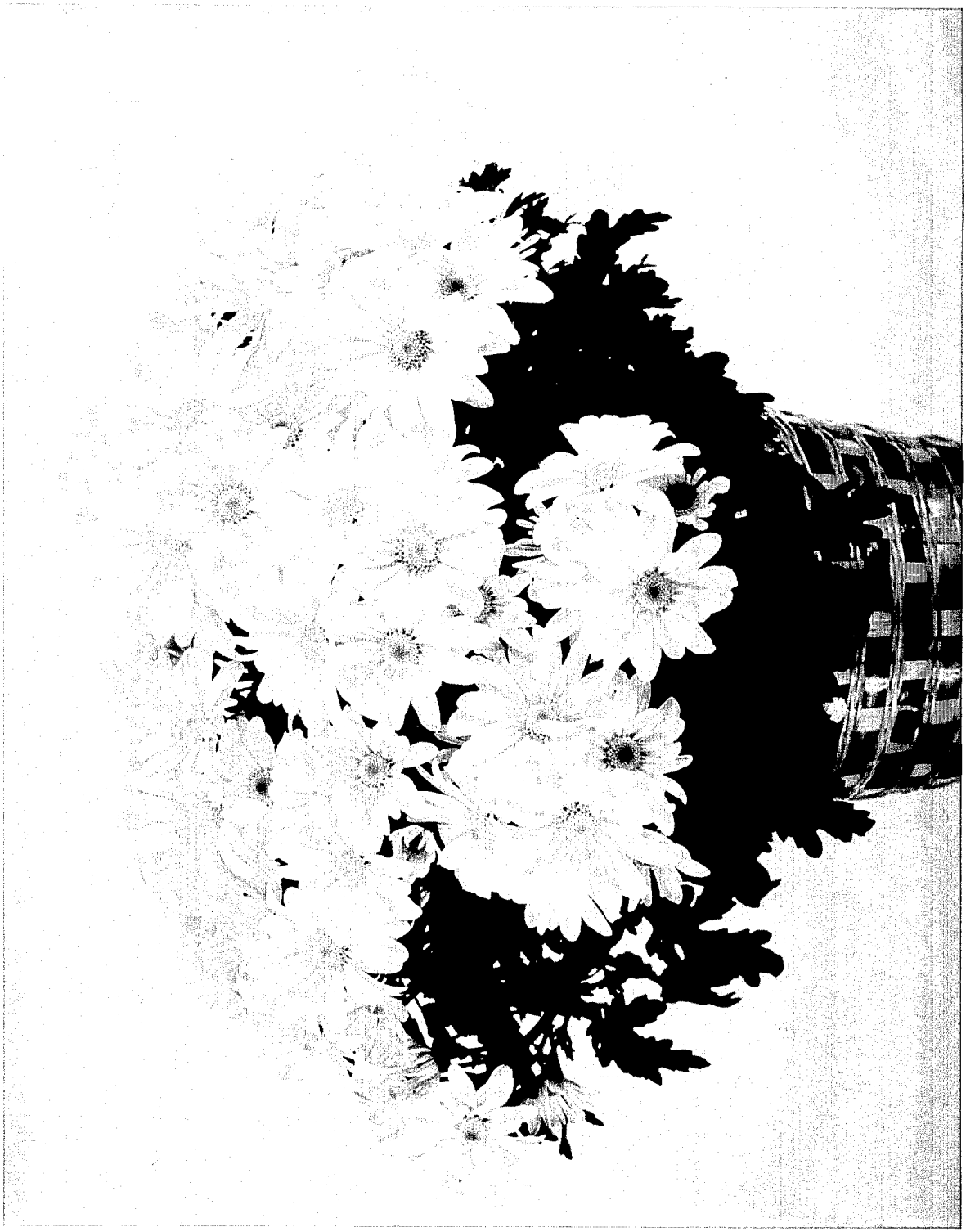

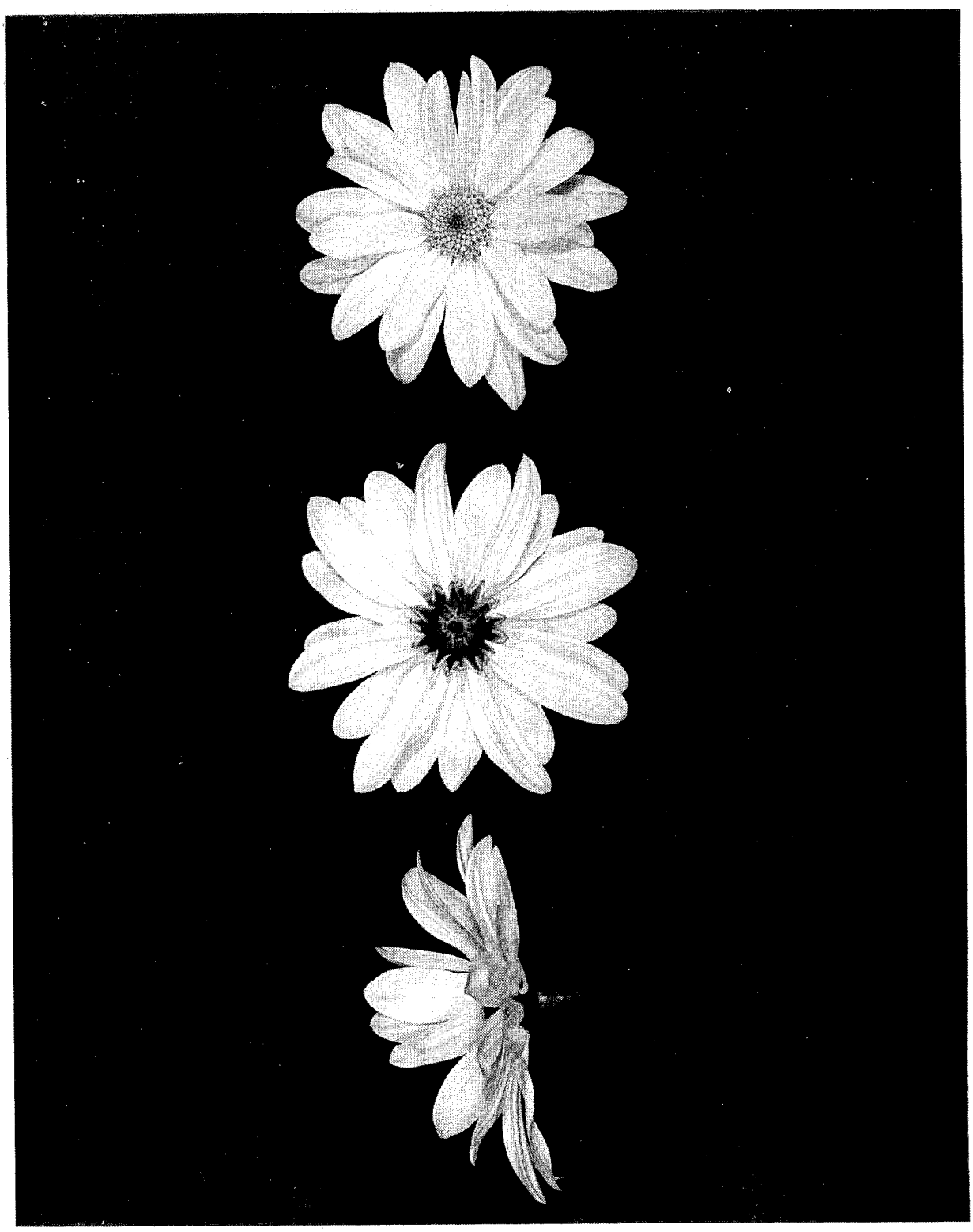

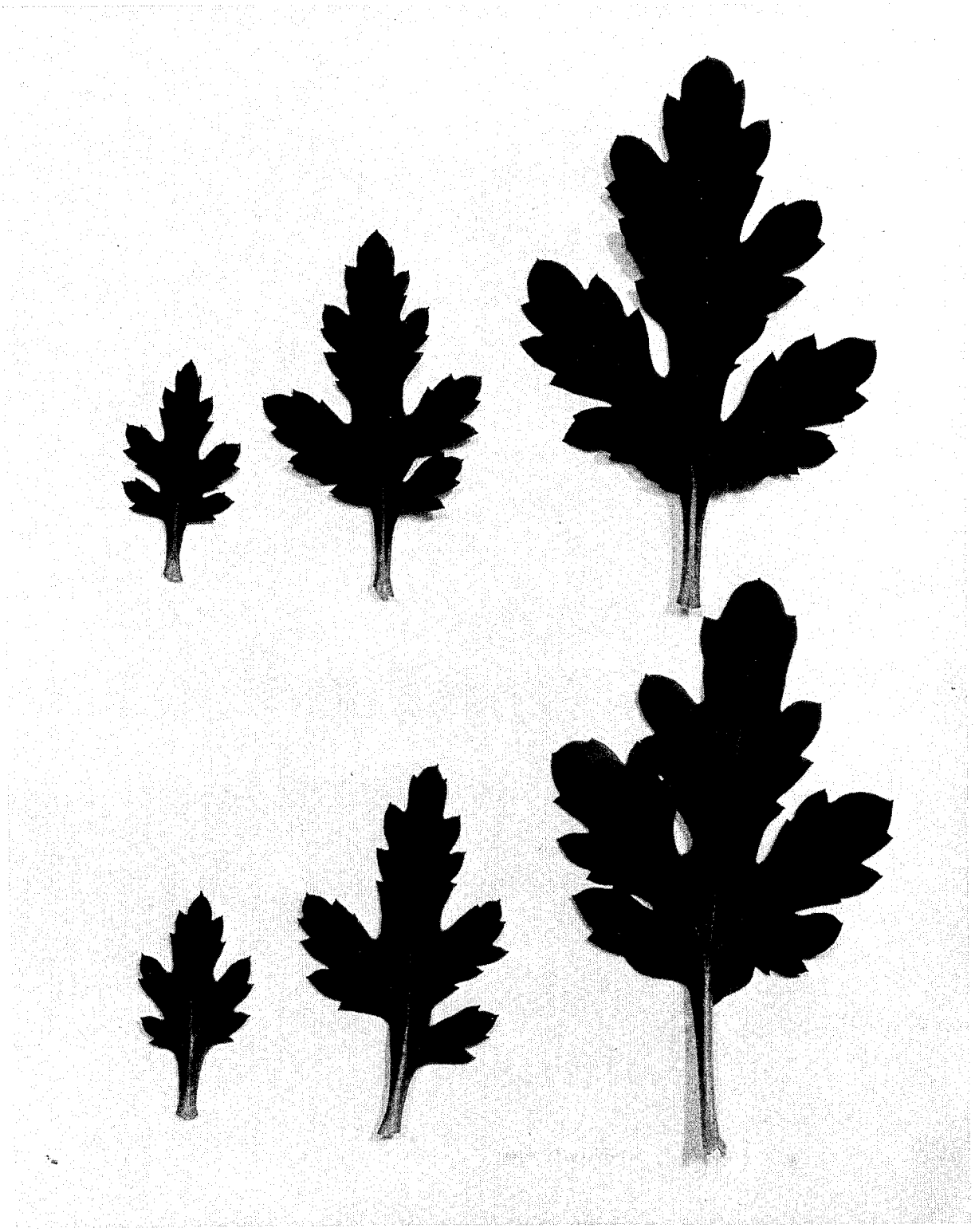

* * * * *